United States Patent [19]

Bicher et al.

[11] 4,369,795
[45] Jan. 25, 1983

[54] IMPLANTABLE MICROTHERMOCOUPLE MEMBER

[76] Inventors: James I. Bicher, 2623 Worchester, West Bloomfield, Mich. 48033; Stanley Frinak, 13711 Victoria, Oak Park, Mich. 48237

[21] Appl. No.: 160,218

[22] Filed: Jun. 17, 1980

[51] Int. Cl.³ .............................................. A61B 10/00
[52] U.S. Cl. .................................... 128/736; 136/230; 374/179
[58] Field of Search ....................... 128/736, 692, 804; 73/359 R, 341

[56] References Cited

U.S. PATENT DOCUMENTS

| | | | |
|---|---|---|---|
| 3,054,397 | 9/1962 | Benzinger | 128/736 |
| 3,466,742 | 9/1969 | Sinclair | 128/692 X |
| 4,182,313 | 1/1980 | Aslan | 128/736 |
| 4,217,910 | 8/1980 | Khalil | 128/692 X |

*Primary Examiner*—Lee S. Cohen
*Attorney, Agent, or Firm*—Garrettson Ellis

[57] ABSTRACT

A microthermocouple member which comprises two wires of dissimilar materials joined together into a thermocouple junction, the wires having diameters of no more than about 75 microns. The wires and junction are carried by an elongated, thin support member, particularly surgical suture material, which is thin enough to be capable of insertion into living tissue without serious disruption of the local circulation. The support member preferably extends beyond the junction and wires, to permit grasping of the extending support member in a forward-slanted slot of a front-pointed stylet.

10 Claims, 4 Drawing Figures

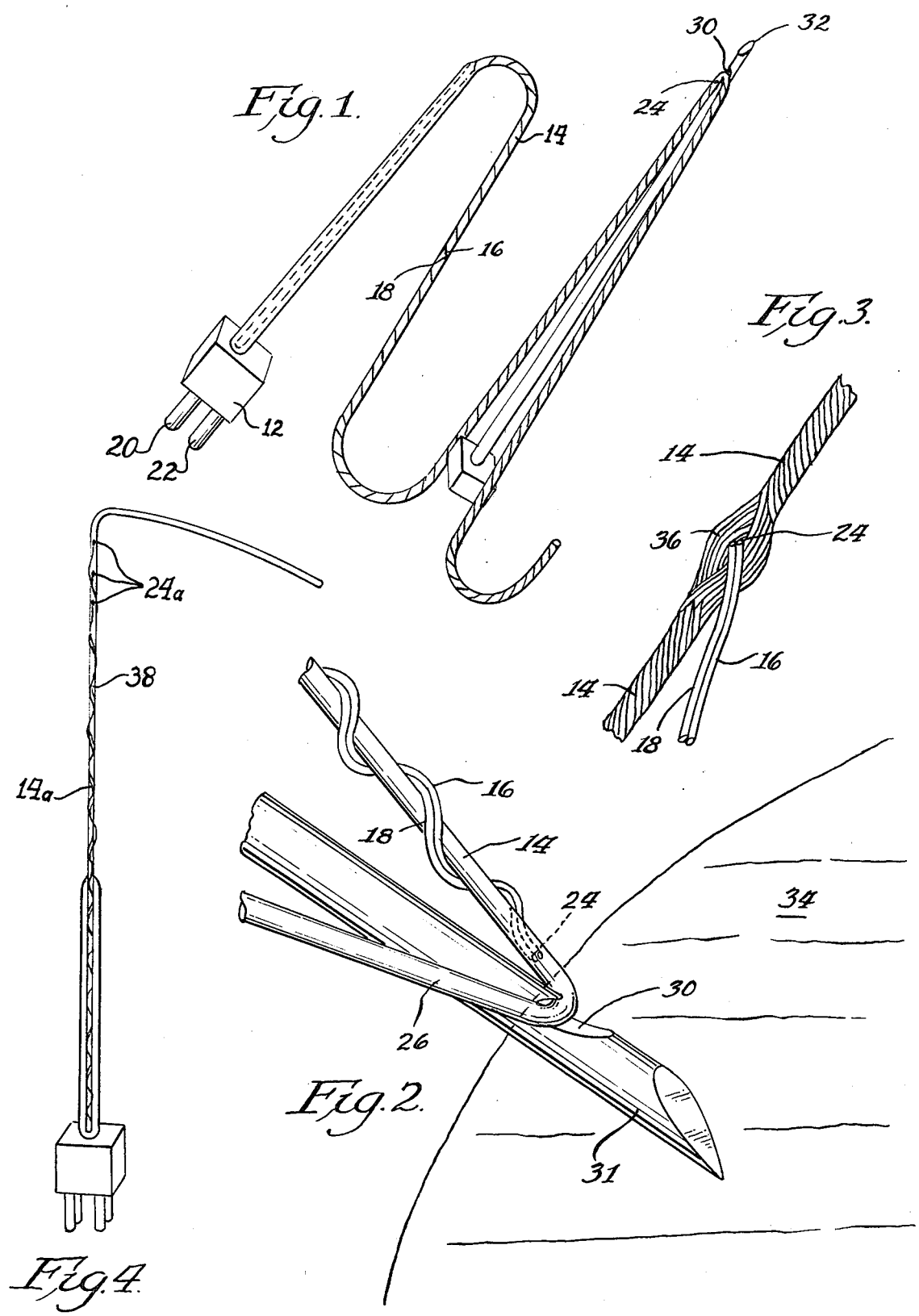

IMPLANTABLE MICROTHERMOCOUPLE MEMBER

BACKGROUND OF THE INVENTION

In the treatment of tumors by irradiation with microwave radiation, the affected tissue is heated by the microwave radiation to an elevated temperature at which the tumor hopefully is killed while the healthy tissue survives.

It is of course critical to monitor the temperature of the tissue during this operation, since too low a temperature will be ineffective against the tumor, and too high a temperature will result in burning of healthy tissue. Thermocouples have been implanted into the tissue which is being irradiated by microwaves to assist in monitoring of the temperatures.

As is well-known, a microthermocouple may be made from a pair of wires of dissimilar metals. For example one wire may be made of copper while the other may be made of the commercially available Constantan alloy. The wires are joined together at one end, and their other ends are connected to a readout apparatus which may directly read out termperature if desired, for example, an apparatus manufactured by the Bailey Instrument Company or other commercially available units.

The thermocouple wires may then be implanted into the desired tissue with the thermocouple wires occupying a metal needle or the like, for measurement of the temperature.

However, the above techniques have resulted in inaccurate temperature readouts because the very presence of a relatively bulky intrusion as represented by the Teflon sheath or other prior art means for implanting the thermocouple can disturb the tissue microcirculation so that the temperature sensed by the thermocouple can be several degrees different from the actual tissue temperature. This is of course undesirable.

Also, tissue implantable thermocouples have utilized relatively large wires of dissimilar metal as has been previously necessary to prevent wire breakage. Relatively large wires having diameters in excess of about 75 microns can pick up significant amounts of the microwave radiation to heat, thus causing burns.

Similarly, thermocouples mounted on the ends of needles or stylets are undesirable because the needle or stylet can readily heat in the presence of microwave irradiation, contributing to burning of the tissue.

In accordance with this invention a microthermocouple member is provided, plus a method for implanting it, in which improved accuracy of temperature readout can be provided, and the wires may be sufficiently small in diameter so that their overheating and burning as the result of exposure to a microwave field is not a problem.

Furthermore, the microthermocouple member and method of this invention may be used in fields other than microwave therapy as may be desired by the user.

DESCRIPTION OF THE INVENTION

In accordance with this invention a microthermocouple member is provided which comprises two wires of dissimilar metals joined together into a thermocouple junction. The wires have diameters of no more than about 75 microns, with the wires and junction being carried by an elongated, thin support member which is thin enough to be capable of insertion into living tissue without serious disruption of the local circulation.

Also, it is preferred for the support member to be non-metallic and thin enough to be relatively inactive in terms of heating in the presence of microwave fields.

It is preferable for the support member to extend beyond the junction and the wires, to permit grasping of the extending support member in a forward-slanted slot of a front-pointed stylet, which may be used to implant the thermocouple member.

Preferably, the support member may be surgical thread or an equivalent thread material having multiple strands, and having a normal diameter of no more than about 400 microns. The surgical thread and the two wires may be twisted, so that the wires are carried by the thread and thereby supported and protected during use.

The microthermocouple is inserted into the tissue of the patient in the following manner.

The support member, and preferably the portion of the support member which extends beyond the junction and the wires, is engaged in a forward-slanted slot in a front-pointed stylet which preferably has a diameter of no more than 0.04 inch, and typically about 0.03 inch. The stylet is then inserted into the tissue, with the result that also a portion of the support member and the thermocouple junction is inserted into the tissue, along with portions of the connecting wires.

Thereafter, the stylet is withdrawn, with the result that the support member slips out of the forward-slanted slot so that the junction and support member portion, along with the corresponding portions of the wires, remain in the tissue.

The two wires are then connected to an appropriate readout device, and the tissue temperature of the patient may be continuously monitored, even during microwave irradiation or during any other procedure as may be desired. The wires are too small to generate significant amounts of heat in response to the microwave radiation, nor does the surgical suture material provide a concentrated response to the microwave irradiation, so that there is no danger of burning of the tissue due to concentration of microwaves about the thermocouple and wires. The stylet of course is removed as stated, so that it has no effect in the microwave field.

The small size of the wires and support member cause essentially no significant disruption of the local circulation, so that tissue reaction is minimal, which contributes to the increased accuracy of the temperature readout of the microthermocouples of this invention.

The microthermocouples may be implanted in the tissue for a period of days or even weeks if desired, with little or no more long term tissue reaction than may be encountered around surgical sutures, stitches and the like.

When it is desired to remove the microthermocouple, it may be gently pulled out of its implanted position by simply pulling on the support member for removal of the entire device from the tissue.

Alternatively, the support member may comprise a Radiopaque Teflon or other plastic thread or thin Teflon sheath about the wires, if desired, with a portion of the Teflon extending beyond the wires and thermocouple for gripping by the forward-slanted slot of the stylet.

It is particularly preferred to manufacture the microthermocouple member of the invention by separating individual fibers in a portion of the surgical thread support member which is used; inserting the microthermocouple junction in between the individual fibers so that the junction is essentially surrounded by fibers; tensioning the thread to retighten the fibers with the junction encased therein, and sealing the fibers and junction with a tissue-compatible adhesive-sealant, for example Eastman 910 Cyanoacrylate Adhesive. After the adhesive has cured, the junction is solidly encased within the thread, being surrounded by the individual fibers thereof.

Referring to the drawings,

FIG. 1 is an elevational view of the microthermocouple member of this invention, installed on a stylet having the forward-slanted slot. In all drawings, the width of the stylet, and of the thread and wires of the microthermocouple member, are transversely enlarged beyong their actual widths for purposes of clarity of the drawing.

FIG. 2 is a detailed, perspective view of the tip of the stylet of this invention, showing details of the microthermocouple member and the stylet tip.

FIG. 3 is an enlarged, detailed perspective view of the microthermocouple junction being inserted in between the individual fibers of said thread prior to the tensioning step, to restore the thread to substantially its initial configuration as described above.

FIG. 4 is a perspective view of an alternative embodiment containing multiple microthermocouple junctions.

Referring to FIG. 1, microthermocouple member of this invention is disclosed, comprising a conventional plug 12, a support member of surgical thread 14, and wound about surgical thread 14 in helical manner a pair of wires 16, 18, each connected to one of prongs 20, 22 of plug 12. Wire 16 may, for example, be made of copper, while wire 18 may be made of Constantan alloy, each of the wires being essentially 50 microns in diameter in this specific embodiment (40 gage wires). The surgical thread support member 14 comprises a substantial number of individual fibers wound together, and may in this specific embodiment be about 250 microns in diameter.

Wires 16, 18 join at thermocouple junction 24, at which point wires 16, 18 typically terminate. Surgical thread 14, however, continues on as an extension 26 of thread 14 for a length of approximately 5 centimeters or so beyond thermocouple junction 24.

This structure, as shown in FIG. 1, may be looped through the forwardly-slanted slot 30 of a stylet 31, which stylet defines a sharp, bevelled pointed end 32 of conventional design.

As shown in FIG. 2, stylet 31 can be inserted into tissue 34 with the extension 26 of surgical thread 14 positioned in forwardly-slanted slot 30, pulling thermocouple junction 34 and the remainder of wire-wound surgical thread 14 after it as stylet 31 is advanced into the tissue to a position where thermocouple junction 24 is located in the tissue desired. Then, stylet 31 may be withdrawn, with the surgical thread extension 26 sliding out of forwardly-slanted slot 30, so that the implanted thermocouple junction 24 remains in its desired position.

Referring to FIG. 3, a fragment of microthermocouple member 10 is illustrated. A portion of surgical thread 14 is uncoiled and fluffed out so that the individual strands 36 form a loose array. Then, the thermocouple junction 24, with the associated wires 16, 18 are inserted into the middle of the array of fibers 36. Following this, surgical thread 14 is pulled to tighten the individual fibers 36 back into a configuration generally approximating the original, tight winding of the fibers in the original thread 14, with the thermocouple junction 24 encased therebetween. The adhesive sealant, such as the Eastman 910 material or alternatively a silicone rubber RTV material, is applied and allowed to cure.

As an additional step, wires 16, 18 may be wound around thread 14, for example, by twisting thread 14 so that the wires 16, 18 form a helical winding. Plug 12 is then attached to the individual wires as shown in FIG. 1.

The resulting microthermocouple member provides improved temperature read-out accuracy of living tissue, since it exhibits only minimal effects on the tissue while it is implanted, contrary to many microthermocouples of the prior art. Furthermore, the thin wire coiled around a preferably non-metallic support member provides little selective absorption of microwaves, so that there is no burning from selective heating of the thermocouple member of this invention. The thermocouple member of this invention is strong due to its preferrred technique of implantation of junction 24 into the midst of the silk surgical suture and due to the winding of thin wires 16, 18 about the suture, so that despite its very thin size, it is strong and durable.

Wires 16 and 18 may be insulated with Teflon or the like.

FIG. 4 is identical to FIG. 1, except that three microthermocouple junctions 24a, each comprising the connection of separate wire pairs 38, are disposed along a surgical thread 14a so that tissue temperature at different depths may be measured.

The above has been offered for illustrative purposes only, and is not intended to limit the invention of this application, which is as defined in the claims below.

That which is claimed is:

1. A microthermocouple member which comprises two wires of dissimilar metals joined together into a thermocouple junction, said wires having diameters of no more than 75 microns; an elongated, thin support thread member; said wires and junction being carried by said elongated, thin support thread member, said member being thin enough to be capable of insertion into living tissue without serious disruption of the local circulation, or causing overheating of the tissue in a microwave field, said support thread member extending beyond said junction and wires to permit grasping of said extending support thread member in a forward-slanted slot of a front-pointed stylet, and means permitting one end of the wires to be connected to recording instrumentation means, said thermocouple junction being carried at an intermediate position on said support thread member.

2. The microthermocouple member of claim 1 in which said support member is surgical thread having a normal diameter of no more than 300 microns.

3. The microthermocouple member of claim 2 in which the individual fibers in a portion of said thread surround said junction, said fibers and junction being sealed with a tissue-compatible adhesive sealant.

4. The microthermocouple member of claim 3 in which said adhesive-sealant is a cyanoacrylate adhesive.

5. The microthermocouple member of claim 4 in which said surgical thread and wires are twisted, whereby said wires are carried by the thread.

6. The microthermocouple member of claim 1 in which multiple similar thermocouple junctions of separate pairs of wires are distributed along the length of said support member, said wire connecting means permitting each junction to be connected to said recording instrumentation means.

7. The method of inserting a microthermocouple into the tissue of the patient, said microthermocouple comprising the junction between two wires of dissimilar metals capable of thermocouple action when joined, said wires having diameters of no more than 75 microns and said junction being joined to a thin, elongated support thread member, which method comprises:

engaging said support thread member in a forward-slanted slot in a front-pointed stylet; inserting said stylet into the tissue, to also insert a portion of said support member and said junction into the tissue, and withdrawing said stylet to cause said junction and support member portion to remain in the tissue.

8. The method of claim 7 in which said thin, elongated support thread member is surgical thread having a normal diameter of no more than 400 microns.

9. The method of claim 7 including the prior steps of separating the individual fibers in a portion of surgical thread, inserting in between said individual fibers a microthermocouple comprising the junction between the two wires of dissimilar metals capable of thermocouple action when joined, said wires having diameters of no more than 75 microns, and winding said wires about said surgical thread in helical manner, tensioning said thread to retighten said fibers with said thermocouple junction encased therein, and sealing said fibers and junction with a tissue-compatible adhesive sealant.

10. The method of claim 9 in which the portion of said support member engaged in said forward-slaned slot is a portion of said support member which extends beyond the junction and wires.

* * * * *